Figure 1:
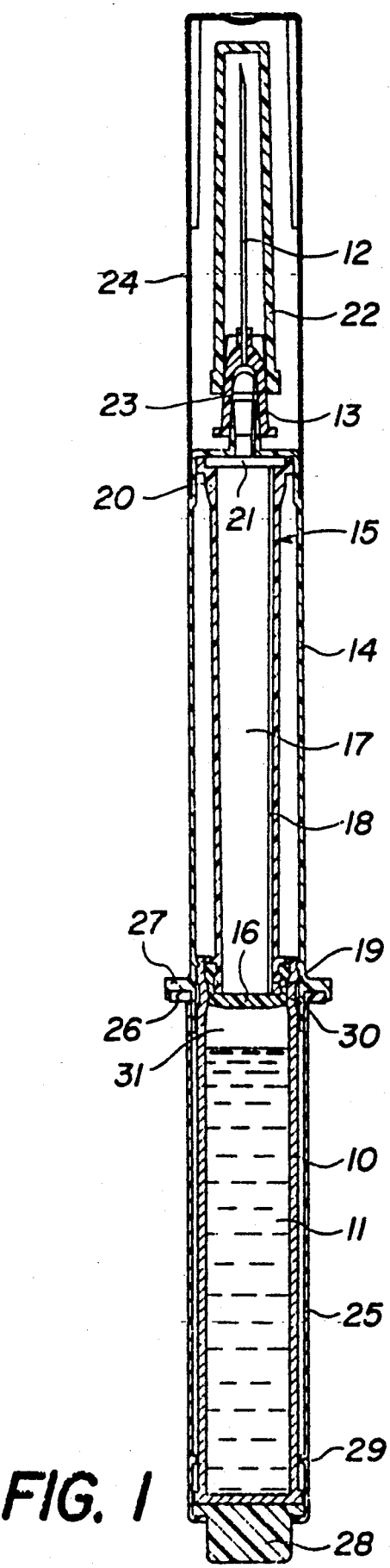

United States Patent [19]

Meyer et al.

[11] Patent Number: 5,015,229
[45] Date of Patent: May 14, 1991

[54] DEVICE FOR DISPENSING LIQUIDS

[75] Inventors: Gabriel Meyer; Ernst Howald, both of Vesenaz, Switzerland

[73] Assignee: Medicorp Holding S.A., Luxembourg

[21] Appl. No.: 392,538

[22] PCT Filed: Nov. 12, 1988

[86] PCT No.: PCT/EP88/01027
§ 371 Date: Jul. 28, 1989
§ 102(e) Date: Jul. 28, 1989

[87] PCT Pub. No.: WO89/04679
PCT Pub. Date: Jun. 1, 1989

[30] Foreign Application Priority Data

Nov. 16, 1987 [CH] Switzerland .................. 4448/87

[51] Int. Cl.⁵ .............................. A61M 5/28
[52] U.S. Cl. ............................. 604/90; 604/184; 604/191; 604/231
[58] Field of Search ............... 604/56, 82, 89–91, 604/181, 184, 187, 191, 197, 218, 231, 232, 207–210; 222/137, 386; 239/320, 330, 331, 333

[56] References Cited

U.S. PATENT DOCUMENTS 4,741,737  5/1988  Meyer et al. ............... 604/231
4,772,271 10/1988  Meyer et al ............... 604/231
4,820,286  4/1989  Van der Wal ............... 604/90

FOREIGN PATENT DOCUMENTS 0150681  8/1985  European Pat. Off. ........... 604/187
 019899  1/1986  European Pat. Off. .
8700163  3/1987  PCT Int'l Appl. .
8404252 11/1984  World Int. Prop. O. ......... 604/187

Primary Examiner—John D. Yasko
Assistant Examiner—Anthony Gutowski
Attorney, Agent, or Firm—Davis, Bujold & Streck

[57] ABSTRACT

A device for dispensing liquids, in particular drugs, comprises a reservoir (11) provided with a neck (30) of reduced cross-section being engaged by a stopper element (16). The reservoir is completely covered by a cap (25) which has at one end a movable push button (28) which abuts against the bottom portion of the reservoir (10). In order to transfer the device from its storage position to its activated position, the operator must press on the push button (28) in such a way that the stopper element (16) penetrates into the interior of the reservoir beyond the neck of reduced crosssection (30). This device can be used as an injection syringe, a spray dispenser, or an applicator for the skin or eyes.

12 Claims, 7 Drawing Sheets

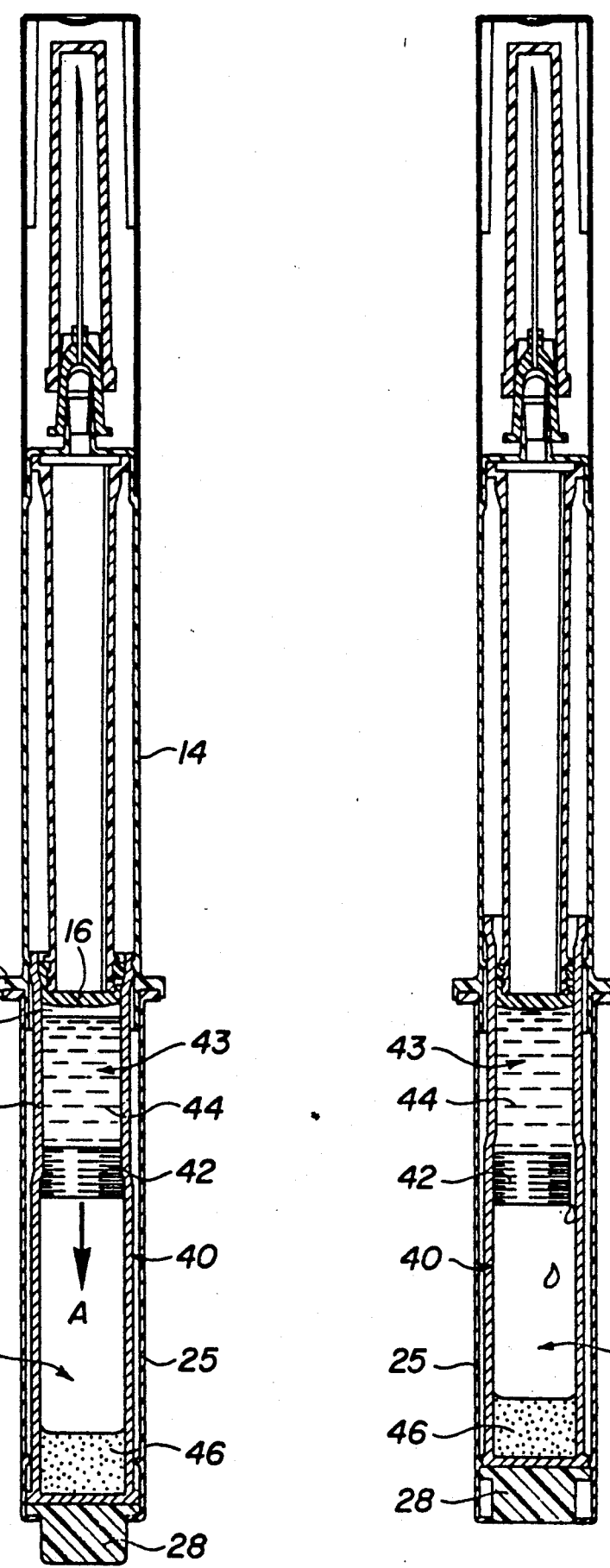

DEVICE FOR DISPENSING LIQUIDS

The present invention concerns a device for the distribution of liquid products, particularly medical substances, comprising an elongated reservoir open at one end and a base closed at its opposite end, substantially cylindrical side walls and a narrowed neck, and containing at least one liquid to be mixed with another substance or to be distributed, for example by spraying, by application to the skin or eyes, or by injection; and a distribution means, movable with respect to this reservoir, this distribution means comprising at least one stopper means, this stopper means, also having a function of piston and valve, being partially engaged in the narrowed neck of the reservoir and being designed to close this reservoir when the device is in a first storage position and to liberate the liquid when the device is in a second activated position, also a capsule solid with this stopper means and mounted on the reservoir so that a protruding section of this reservoir, neighbouring its narrowed neck, is engaged in this capsule; this reservoir being surmounted by a barrel provided with inviolability units keeping it firmly attached to the capsule during storage.

Distributive devices of this type which are generally designed to be stored over a period of time which may be relatively long, already exist. To this end, the stopper means comprises a head of elastomer which is strongly compressed in the interior of the narrowed neck of the reservoir. This stopper means also comprises elastic retaining means which help to keep it in position and prevent any movement towards the interior of the reservoir. In addition the interior of this reservoir is subject to a slight positive pressure which also opposes a force tending to prevent the stopper means accidentally penetrating the interior of the reservoir during the entire storage period. It follows from this, that to bring the stopper means from the position it occupies in the storage position to the position it occupies when it is in the activated position, it is necessary to exert a certain force capable of overcoming these initial constraints. If this force is exerted without control or restraint, a part of the liquid initially contained in the reservoir risks being ejected and lost. Given that the volume of liquid contained in the reservoir is accurately proportioned, it is essential, especially when a medicine is involved, for example a medicine to be injected, that a part of this liquid should not be lost during the manipulations described above.

The present invention proposes solving this problem by providing, in particular, means of allowing the precise control of the transformation of the device from its storage position to its activated position.

To this end, the device is characterised in that the barrel is provided with a plunger which is designed to push against at least one part of the closed base of the reservoir and/or against its side walls, and which is designed to push the reservoir in such a way that the stopper means enters the neck and the device passes from its storage position to its activated position, this plunger being a piece moving axially with respect to said barrel.

According to a preferred embodiment of the device, the distribution means is the needle of a syringe and the liquid to be distributed is an injectable medicine.

According to another preferred embodiment of the invention, the distribution means is an applicator for the skin, the eyes or of a spray, and the liquid is a substance to be applied to the skin, the eyes or by spraying.

To enable the path of the plunger to be limited and, from this ensure a precise control of the movement of the reservoir to transform the device from its storage position to its activated position, the barrel is preferably fitted with at least one stop.

For certain applications, the quantity of liquid contained in the reservoir no longer corresponds to a single dose but to a volume which may correspond to several multiples of a single dose. In this case the barrel would preferably bear two stops designed to define the path of the plunger for each dose of liquid to be distributed and means of ensuring a controlled axial displacement of the barrel to bring the plunger back to its initial position after each distribution of a dose of liquid.

These means destined to ensure the controlled axial displacement of the barrel preferably comprise an internal thread of its barrel and a complementary element designed to engage in this thread, which is solid with the capsule.

In the case where the reservoir comprises a unique dose of a single liquid to be distributed, the path of the plunger is preferably equal to the axial displacement of the reservoir, with respect to the stopper means, necessary to bring the first drop of the liquid to an extremity of distribution of the distribution means. In the case of a syringe this operation is commonly known as the "debullage" of the syringe.

In the case where the reservoir comprises two compartments separated by a second stopper means and where the compartment situated between the stopper means and the intermediate stopper means, and corresponding to the narrowed neck of the reservoir, contain a liquid destined to be mixed with a substance contained in the second compartment, situated between the second stopper means and the base of the reservoir, the path of the plunger is preferably equal to the axial displacement of the reservoir, with respect to the first stopper means, necessary to ensure the ejection of the intermediate stopper means from the narrowed neck so as to permit the passage of the liquid from the first compartment to the second compartment.

In this example of an embodiment, the second compartment preferably contains a substance to be mixed with the liquid of the first compartment.

According to a particular embodiment, this substance is a lyophilisate.

In the case where the reservoir comprises two compartments, the plunger may comprise a substantially cylindrical lateral tubular section positioned between the external side walls of the reservoir and the interior side walls of the barrel and the length of this tubular side section corresponds to the path of the reservoir required to make the intermediate stopper means press against the stopper means and to make the stopper means partially enter the second compartment.

In this case equally, the lateral tubular section of the plunger may have an internal diameter substantially equal to the exterior diameter of the part of the reservoir corresponding to the second compartment.

Figure 2:
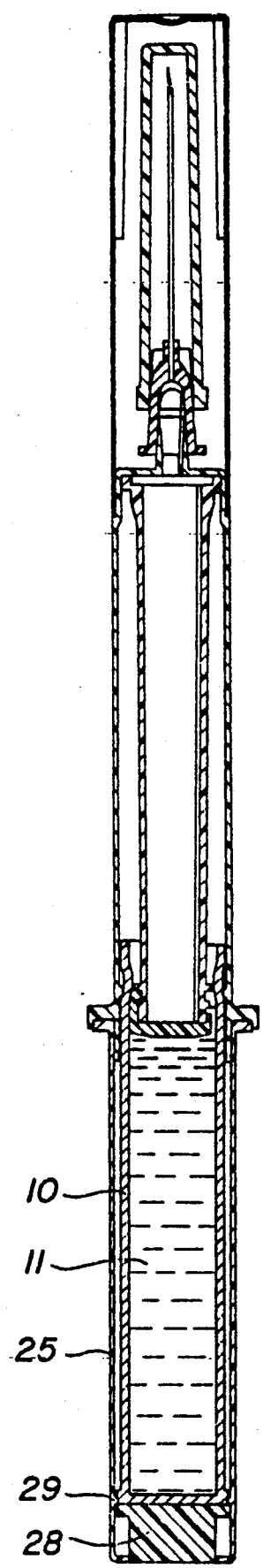
Figure 5:
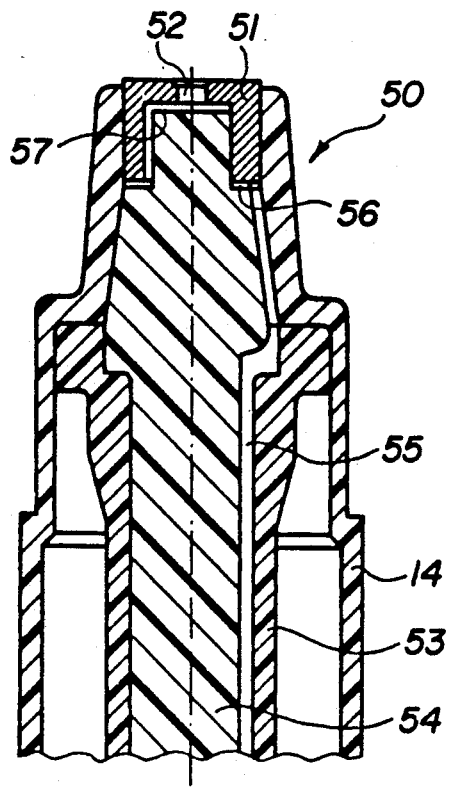
Figure 6:
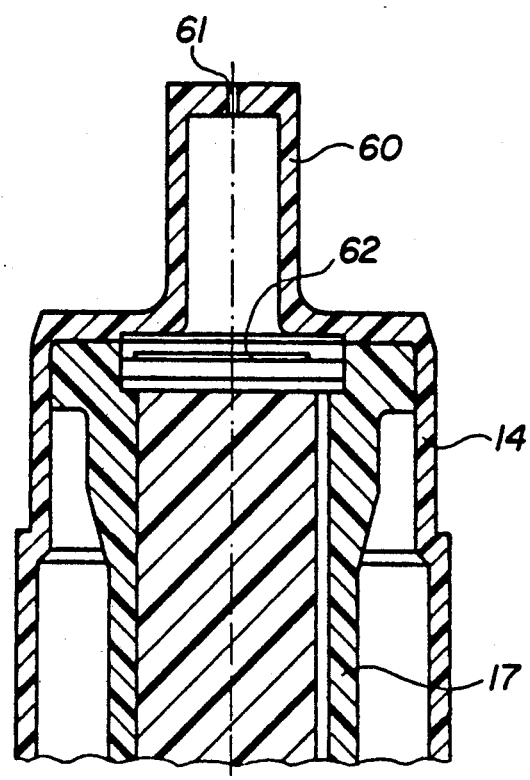
Figure 9:
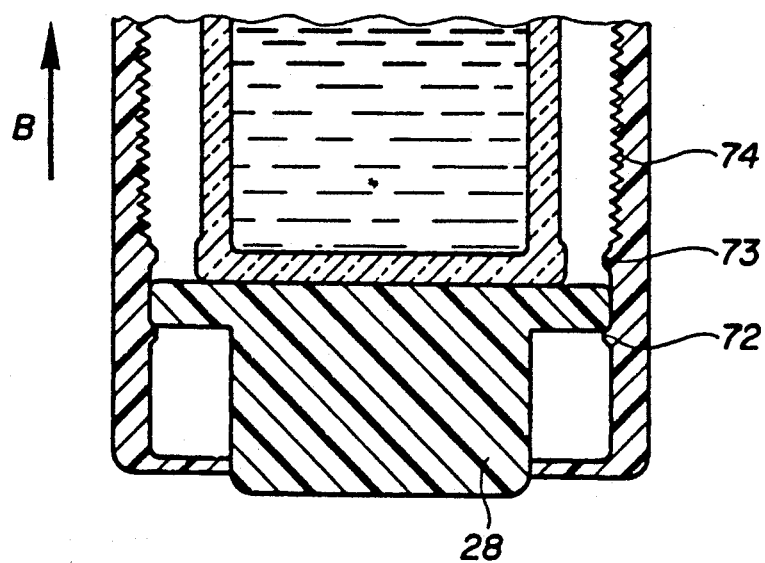
Figure 7:
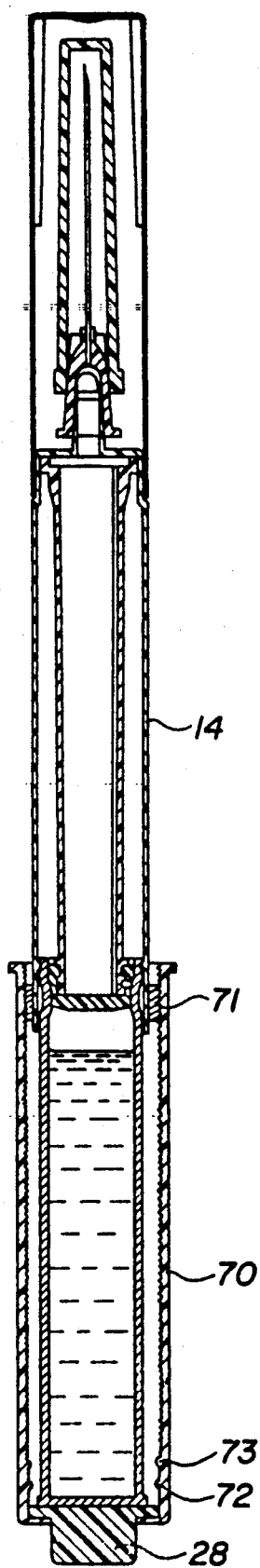
Figure 8:
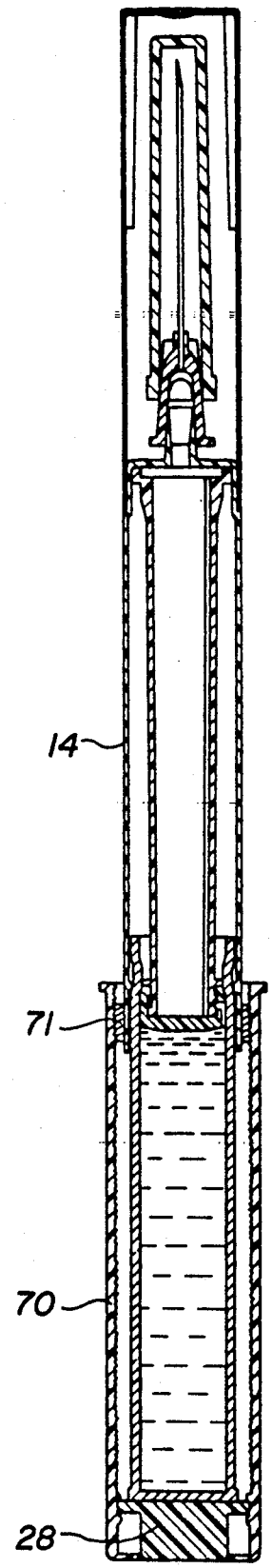
Figure 10:
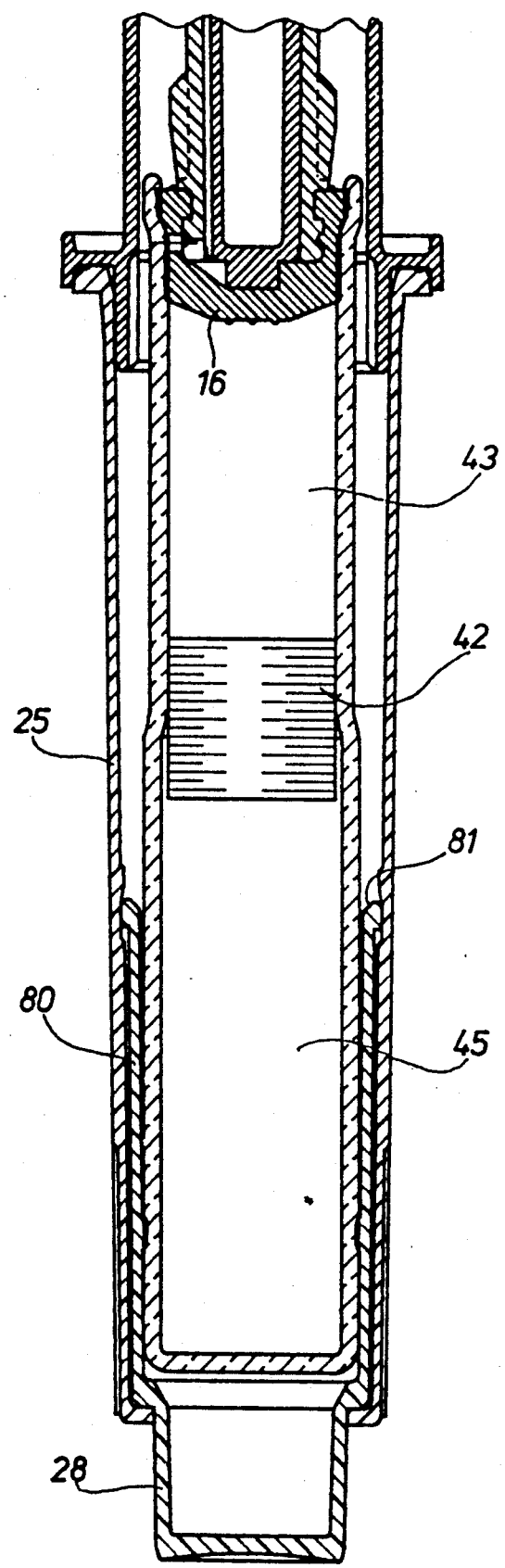
Figure 11:
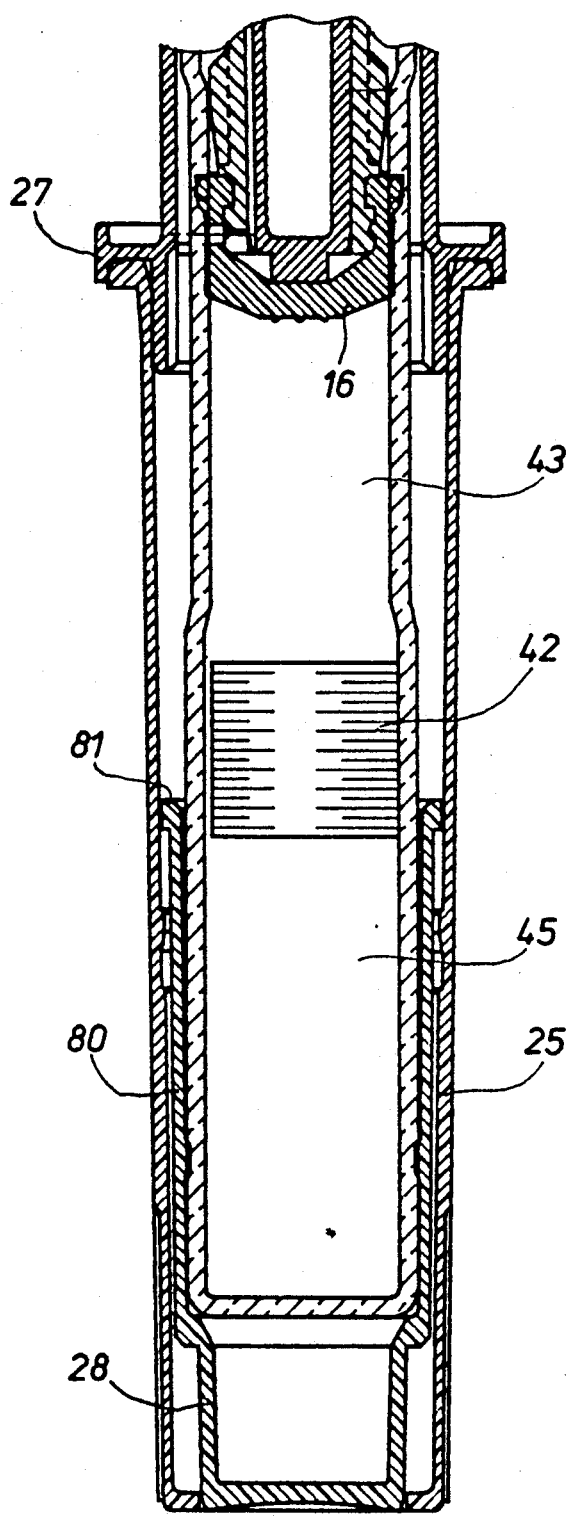
Figure 12:
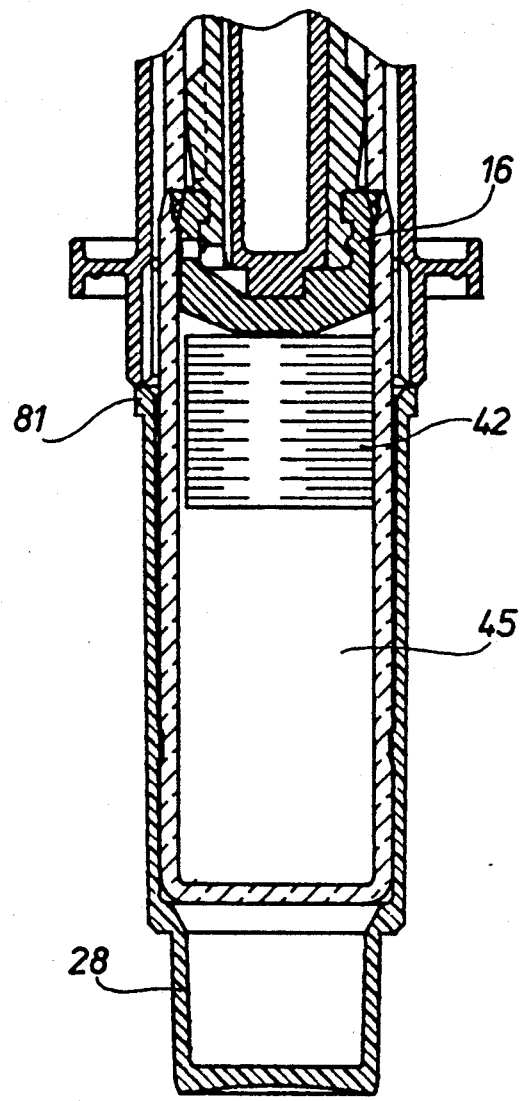

The present invention will be better understood by referring to the description of an example of the embodiment and to the annexed drawings in which:

FIG. 1 represents a view of an axial cross-section of a first form of an embodiment of an injection syringe in the storage position, FIG. 2 represents the same syringe in the activated position, FIG. 3 represents a second example of a syringe shown in axial cross-section and in the storage position, FIG. 4 represents the same syringe in the activated position, FIG. 5 shows an enlarged view of the tip of a nasal spray of a device according to the invention, FIG. 6 represents an enlarged view of a tip of a dropper adapted for the end of a device according to the invention, FIG. 7 shows an example of a multidose syringe corresponding to a device according to the invention, in the storage position, FIG. 8 shows the same syringe in the activated position, FIG. 9 represents an enlarged view of a part of the syringe represented by FIGS. 7 and 8, FIG. 10 represents a partial view of a variant of the syringe of FIGS. 3 and 4, shown in the storage position, FIG. 11 shows the syringe of FIG. 10 during the phase of transfer of the liquid from the first compartment towards the second compartment, and FIG. 12 represents a partial view of the syringe of FIGS. 10 and 11 in a phase immediately preceding their use.

With reference to FIGS. 1 and 2, the syringe represented respectively in the storage and activated state essentially comprises a reservoir 10 containing a liquid medicine 11 to be injected by means of a needle 12 fixed on an end needle-bearer 13 solid with a capsule 14. The capsule 14 carries a distribution means 15 which is equipped with a stopper means designed to fulfil the functions of stopper means as stated and of piston-valve during a later phase. The stopper means 16 is mounted on one end of a central rod 17 provided with an axial canal 18 which communicates with a radial canal 19. The central rod 17 is fixed by means of a base 20 at one end of the capsule 14 so as to firmly hold a membrane filter 21 on which the axial canal 18 opens out.

The needle 12 is protected by a hood 22 which engages directly with a needle-support 23. An over-hood 24 whose diameter is substantially equal to the diameter of the capsule 14, is mounted on the end of this latter to cover the needle 12 and its hood 22.

A barrel 25 entirely surrounds the reservoir 10. At one end, the barrel 25 bears ridges 26 which engage in an annular depression in the flanges 27 which form part of the capsule 14. The inviolability of the system is ensured by linking the ridges 26 with the flanges 27 by ultrasonic welding. At its other end, the barrel 25 is open and provided with a push button 28 whose base presses against the base of the reservoir 10. The barrel 25 bears one or several internal stops 29 whose function is to limit the path of the push button 28.

In the storage position, the stopper means 16 is partially engaged in the narrowed neck 30 of the reservoir 10. In this way the radial canal 19 is blocked and no matter what the position of the syringe the liquid medicine 11 cannot run in the direction of the needle 12. However a certain volume of air 31, slightly compressed, is present above the liquid 11. To put the syringe into its activated state, it suffices to push the stopper means 16 into the reservoir 10 so that the opening of the radial canal 19 moves to the wide part of the reservoir, i.e. above the narrowed neck 30. To do this it is necessary to overcome the forces due to the elastic resistance from the compression of the stopper means 16, made out of an elastomer material and to compress the volume of air 31 contained in the reservoir 10. As mentioned in the introduction, the force applied to overcome these resistances is relatively large and must be applied to the base of the reservoir 10 so as to produce a movement of the stopper means 16 relative to the reservoir. In addition it is necessary that the forces be applied in a controlled way to avoid the stopper means penetrating the reservoir too deeply and that a part of the liquid does not accidentally escape via the radial canal 19, the axial canal 18 and the needle 12. To avoid this risk, the barrel 25 is provided with a push button 28 and at least one stopper 29 which limits the path of the push button 28. This path is determined so that it corresponds with the required displacement of the reservoir 10 with respect to the stopper means 16, this displacement being sufficient to expel air from the needle and eventually make the first drop of liquid to be injected appear at the tip of the needle.

When this operation is finished, the barrel 25 may be removed, together with the hoods 22 and 24 and the operator may perform the injection.

FIG. 2 represents the syringe in the activated position after the push button 28 has been pushed in as far as the stop 29. This figure clearly shows that the volume of air 31 has been evacuated and that the syringe is almost ready to inject, on condition each time that the barrel 25 and the hoods 22 and 24 are removed.

The syringe illustrated by FIGS. 3 and 4, in storage position and activated position respectively, differs from that shown in FIGS. 1 and 2 in that the reservoir 40 is of a type which has a double compartment. This reservoir comprises a relatively long, narrowed neck 41 which is blocked at the open end of said reservoir by a stopper means 16 of elastomer identical to that of the syringe of FIGS. 1 and 2, and at the other end by a second stopper means 42, which will be known as the intermediate (intermediary) stopper means, also made from elastomer. The first compartment 43, delimited on one hand by the wall of the narrowed neck 41 and on the other hand by the stopper means 16 and the intermediate stopper means 42, contain a liquid 44 which is to be mixed with a substance in the second compartment 45 delimited on the one hand by the widened out interior wall of the reservoir 40 and on the other hand by the intermediate stopper means 42 and the base of said reservoir 40. In the present case the substance contained in the second compartment 45 is a lyophilisate 46 and the liquid 44 contained in the first reservoir is a solvent intended to dissolve the lyophilisate.

In its storage position, the intermediate stopper means hermetically separates the two compartments 43 and 45. In a first phase of use, the operator must be able to push back the intermediate stopper means 42 out of the narrowed neck so that the solvent 44 is freed and allowed to run into the second compartment to dissolve the lyophilisate 46. Towards this end, the operator pushes the push button 28 which displaces the reservoir 40 with respect to the stopper means 16 which penetrates further forward in the interior of the narrowed neck 41. After a first phase of compression of the volume of gas 31 above the liquid 44, the pressure exerted on the contents of the first compartment 43 by the stopper means 16 is entirely transmitted to the intermediate stopper means 42 which moves in the direction of the arrow A. The path of the push button 28 is determined so that the displacement of the intermediate stopper means 42 is sufficient to release the solvent 44. The mixing or the dissolution of lyophilisate may proceed and the syringe will be ready to perform an injection after the removal of the barrel 25, following the rupture of its inviolability links with the flanges 27 of the capsule 14, and the operation of expelling air from the needle which consists of displacing the reservoir in such a way as to bring the intermediate stopper means 42 in contact with the stopper means 16 and to make this latter penetrate the second compartment.

In this example of an embodiment, the push button 28 ensures a displacement which is limited but sufficient to activate the syringe while avoiding an accidental ejection of part of the solvent 44 before it has had time to run in to the second compartment to dissolve the lyophilisate.

FIG. 5 shows a partially cut away view of another embodiment of a distribution device which is equipped with a nasal spray tip 50. In this example of an embodiment, the capsule 14 carries at its end a piece 51 provided with an opening 52 containing a spray nozzle. The support 53 of the stopper means (not shown) has a tubular shape and contains a solid internal cylinder 54 designed to define an axial canal 55 which opens onto a ring-shaped opening 56 arranged around the inside edge of the piece 51, and which is connected to a canal 57 opening onto the spray nozzle 52. The functionning of this device is substantially identical to that described with reference to FIGS. 1 and 2. The act of pressing the plunger (not shown) causes the activation of the device, i.e. the penetration of the stopper means into the corresponding reservoir.

FIG. 6 shows another example of the distributive device which in this case is equipped with a dropper tip. In this case the end of the capsule 14 comprises a narrowed tip 60 which has a central hole 61. A membrane type filter 62 may be placed between the tip 60 and the base of the support 17 of the stopper means (not represented).

FIGS. 7 and 8 show a distributive device, which in this case, is an injection syringe of the multidose type. This device is characterised, with respect to the syringes represented by FIGS. 1 and 2, by the existence of a barrel 70 having an interior thread which screws onto a complementary component 71 having an external thread and which is fixed to the superior end of the capsule 14, the aim of this device being to allow the controlled relative displacement of the barrel 70, with respect to the capsule 14.

In the storage position represented by FIG. 7, the push button 28 is in its outermost position. To activate the system the push button must be pushed past a first stop 72 up to a second stop 73. This operation is illustrated by FIG. 8. The plunger is thus pushed completely inside the barrel 70 and the syringe is activated, i.e. air is expelled from the needle and it is ready for use. In this case, the operator does not remove the barrel 70 contrary to the procedure carried out with the barrel 25 of the syringe of FIGS. 1 and 2, but screws this barrel on the threaded component 71, which has the effect of displacing it in the direction of the arrow B as shown in FIG. 9. This relative displacement pushes the push button 28 against the first stop 72. In this position the syringe is ready for the injection of a first dose. This first dose corresponds to the displacement of the push button between the first stop 72 and the second stop 73. After this first injection, the operator again screws the barrel 70 on the threaded component to bring the push button 28 back to its outermost position, thus reactivating the system and making it ready for the injection of the following dose.

It is understood that this principle does not apply only to applicators of the syringe type, but also to all other forms of distributive devices such as sprays, drop applicators etc.

Also, the interior thread 74 may be replaced by a structure equivalent from the operational point of view such as a spiral groove or a similar groove.

With reference to FIGS. 10 to 12, the syringe of the mixing type or with two compartments 43 and 45 is identical to that of FIGS. 3 and 4, except where the shape and the function of the stopper means 16 is concerned. As before, it comprises a stopper means 16 which fulfils the roles of a stopper means, and of a piston and a valve, and an intermediate stopper means 42 which separates the first compartment 43 from the second compartment 45.

The barrel 25 comprises an opening in which the push button 28 engages. This latter comprises a substantially cylindrical section 80 which is engaged between the external side walls of the reservoir and the internal side walls of the barrel. The axial length of this section is calculated so that the push button ensures its new functions resulting from the above description.

In its storage position, the push button 28 and the barrel 25 occupy the relative position shown by FIG. 10. Initially, the operator pushes the base of the push button 28 into the barrel whose base is pressed against the flanges 27 of the device. This has the effect of making the stopper means 16 penetrate the narrowed neck of the first compartment 43 and of making the intermediate stopper means 42 penetrate the second compartment. The liquid of the first compartment may thus run into the second compartment. This phase is illustrated by FIG. 11. At this moment the operator removes the barrel 25 and pushes the plunger until the free edge 81 of the cylindrical section 80 comes to rest against the edge of the capsule (FIG. 12). All the liquid of the first compartment 43 has been transferred in its entirety to the second compartment 45. The intermediate stopper means 42 is brought into contact with the stopper means 16. This latter has partially penetrated the second compartment, i.e. the enlarged section of the reservoir. After the release of the push button 28, the injection may take place.

This device is particularly interesting for the user because it permits an almost automatic "preparation" of the syringe by elementary manipulations.

We claim:

1. A device, for distributing a liquid medical product, comprising an elongated reservoir being open at one end and being closed at an opposite end thereof, the reservoir having substantially cylindrical side walls and a neck of reduced cross-section adjacent the open end, the reservoir being suitable for containing at least one liquid to be distributed by the device; distribution means, movable with respect to the reservoir, for distributing the liquid from the reservoir along an axial channel thereof to a dispensing element located remote from the reservoir, said distribution means comprising movable stopper means, at least partially engaging the neck of the reservoir, for sealing the open end of the reservoir when the device is in a storage position, and a radial channel communicating with the axial channel and located adjacent said stopper means remote from the closed end, said radial channel being closed by said stopper means when the device is in a storage position and communicating with the reservoir when the device is in an activated position to allow the flow of liquid from the reservoir to the dispensing element via the axial channel; a capsule, attached to the distribution means, engaging the open end of the reservoir; and a barrel, surmounting the reservoir, provided with inviolability means for keeping the barrel firmly attached to the capsule during storage; characterised in that said barrel is provided with a push button located to push against a portion of the closed end of the reservoir in such a way that the closed end of the reservoir moved toward said stopper means and the device passes from its storage position to its activated position, and said push button moves axially with respect to said barrel.

2. A device according to claim 1, characterised in that the distribution element is a syringe needle and that the liquid to be distributed is an injectable medicine.

3. A device according to claim 1, characterised in that the dispensing element is an applicator for applying the liquid of one of the skin and the eyes by spraying.

4. A device according to claim 1, characterised in that said barrel carries at least one stop to limit the motion of the push button.

5. A device according to claim 1, in which the reservoir contains several doses of liquid to be distributed, characterised in that said barrel carries two stops which define the path of the push button for each dose to be distributed, and means for ensuring a controlled axial movement of the barrel to bring the push button back into its initial position after each distribution of a dose of liquid.

6. A device according to claim 5, characterised in that the means of ensuring a controlled axial movement of the barrel compise an interior thread on said barrel and complementary means, integral with and carried by an exterior surface of the capsule, for engaging the interior thread and providing the controlled axial movement.

7. A device according to claim 1, in which the reservoir contains a single dose of a single liquid to be distributed, characterised in that the path of the push button equals the axial displacement of the reservoir, with respect to said stopper means, necessary to bring a first drop of the liquid to the dispensing element.

8. A device according to claim 1, in which the reservoir comprises first and second compartments separated by an intermediary stopper and in which the first compartment defined between said stopper means and the intermediary stopper, including the neck of the reservoir, contains a liquid to be mixed with a substance contained in the second compartment defined between the intermediary stopper and the closed end of the reservoir, characterised in that the path of the push button is equal to the axial displacement of the reservoir, with respect to said stopper means, necessary to eject the intermediary stopper into the second compartment and allow passage of the liquid from the first compartment into the second compartment.

9. A device according to claim 8, characterised in that the second compartment contains the substance to be mixed with the liquid from the first compartment.

10. A device according to claim 9, characterised in that the substance in the second compartment is a lyophilisate.

11. A device according to claim 8, characterised in that said push button comprises a cylindrical section positioned between an exterior surface of the side walls of the reservoir and an interior surface of side walls of the barrel and in that the length of this cylindrical section corresponds to the path of the reservoir required to make said stopper means press against the intermediate stopper and partially penetrate the second compartment.

12. A device according to claim 11, characterised in that the cylindrical section of the push button has an interior diameter substantially equal to the exterior diameter of the part of the reservoir corresponding to the second compartment.

* * * * *